US011099178B2

(12) United States Patent
Matthias et al.

(10) Patent No.: US 11,099,178 B2
(45) Date of Patent: *Aug. 24, 2021

(54) DEVICE AND METHOD FOR DETECTING SUBSTANCES PRESENT IN BIOLOGICAL OR CHEMICAL SAMPLES

(71) Applicant: Torsten Matthias, Wendelsheim (DE)

(72) Inventors: Torsten Matthias, Wendelsheim (DE); Hans-Peter Schimon, Heiningen (DE); Jens Blecken, Fuerfeld (DE); Markus Wulf, Alzey (DE)

(73) Assignee: Torsten Matthias, Wendelsheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/354,910

(22) PCT Filed: Oct. 29, 2012

(86) PCT No.: PCT/EP2012/004526
§ 371 (c)(1),
(2) Date: Apr. 28, 2014

(87) PCT Pub. No.: WO2013/060482
PCT Pub. Date: May 2, 2013

(65) Prior Publication Data
US 2014/0315226 A1 Oct. 23, 2014

(30) Foreign Application Priority Data

Oct. 28, 2011 (DE) .......................... 10 2011 117 320
Oct. 26, 2012 (EP) ................... PCT/EP2012/004490

(51) Int. Cl.
*G01N 33/543* (2006.01)
*G01N 35/00* (2006.01)
*G01N 35/02* (2006.01)

(52) U.S. Cl.
CPC ....... *G01N 33/54306* (2013.01); *G01N 35/00* (2013.01); *G01N 35/028* (2013.01)

(58) Field of Classification Search
None
See application file for complete search history.

(56) References Cited

U.S. PATENT DOCUMENTS 4,474,892 A * 10/1984 Murad ............. G01N 33/54306
436/513
4,873,633 A * 10/1989 Mezei .................... G01N 33/80
356/39
5,545,531 A * 8/1996 Rava .................... B01J 19/0046
435/6.14
5,798,263 A * 8/1998 Wood .................... G01N 21/763
250/361 C
5,985,218 A * 11/1999 Goodale ................. B01L 3/508
206/569
6,083,763 A * 7/2000 Balch .................... B01J 19/0046
422/105
6,252,664 B1 * 6/2001 Barbera-Guillem ... G01N 21/59
250/461.1
6,556,299 B1 * 4/2003 Rushbrooke ....... G01N 21/6452
250/458.1
6,746,864 B1 * 6/2004 McNeil ............... G01N 33/5302
356/417
7,480,042 B1 * 1/2009 Phillips ................ G01N 21/278
356/243.1
8,142,719 B2   3/2012 Matthias et al.
9,918,640 B2 * 3/2018 Ntziachristos ..... A61B 1/00009
2003/0082551 A1 * 5/2003 Zarling .................. C40B 50/06
435/6.16
2004/0029213 A1 * 2/2004 Callahan .............. G06K 9/4609
435/40.5
2004/0189311 A1 * 9/2004 Glezer ................... G01N 21/76
324/444
2005/0095698 A1 * 5/2005 Carlson .............. G01N 21/6445
435/287.2
2005/0175504 A1 * 8/2005 Tanoshima .......... G01N 35/0099
422/67
2005/0227360 A1 * 10/2005 Devlin, Sr. ........ G01N 35/0092
436/45
2006/0194308 A1 * 8/2006 Gutekunst ................ G01J 3/021
435/288.7
2007/0177778 A1 * 8/2007 Massaro ............ G01N 35/1016
382/128
2007/0212689 A1 * 9/2007 Bianchi ................ C12Q 1/6883
435/6.11

(Continued)

OTHER PUBLICATIONS

The International Search Report and Written Opinion, dated Mar. 22, 2013, in the related PCT Appl. No. PCT/EP12/04526.

*Primary Examiner* — Ann Y Lam
(74) *Attorney, Agent, or Firm* — Buchanan Ingersoll & Rooney PC

(57) ABSTRACT

The present invention relates to a device and a method for detecting substances which are present in biological or chemical samples, each substance producing an optically detectable signal upon reaction with a reagent. The device further comprises a sample carrier with at least two receptacles for receiving samples and is characterized in that at least part of the receptacle is equipped to receive at least 2 reagents each, and in that a camera for recording an image which shows at least one receptacle filled with at least two reagents for the detection of different substances, and an evaluation device for evaluating the samples which device is designed such as to evaluate each image by analyzing the signals in the image. Said method comprises the following steps: Introducing at least two reagents into one receptacle of a sample carrier, and optionally immobilizing the reagents, adding the sample to the receptacle, recording an image by means of a camera such that the image shows the receptacle which is loaded with at least two reagents, and evaluating the image by analyzing the color spectrum of the samples in the image.

18 Claims, 1 Drawing Sheet

(56) References Cited

U.S. PATENT DOCUMENTS

| | | | |
|---|---|---|---|
| 2008/0207461 A1* | 8/2008 | Ermantraut | B01J 19/0046 506/8 |
| 2008/0274905 A1* | 11/2008 | Greene | G01N 21/6428 506/4 |
| 2008/0317325 A1* | 12/2008 | Ortyn | G01N 15/1475 382/133 |
| 2009/0131269 A1* | 5/2009 | Martin | C12Q 1/6834 506/9 |
| 2009/0247414 A1* | 10/2009 | Obradovic | C12Q 1/6874 506/3 |
| 2010/0030069 A1* | 2/2010 | Peter | A61B 6/037 600/427 |
| 2010/0216143 A1* | 8/2010 | King | G01N 21/6428 435/6.13 |
| 2010/0232675 A1* | 9/2010 | Ortyn | G01N 15/1475 382/134 |
| 2011/0059870 A1 | 3/2011 | Wohlstadter et al. | |
| 2011/0105354 A1 | 5/2011 | Glezer et al. | |
| 2011/0143947 A1* | 6/2011 | Chamberlin | G01N 21/6452 506/7 |
| 2011/0216953 A1* | 9/2011 | Callahan | G06K 9/00 382/128 |
| 2012/0061259 A1* | 3/2012 | Lin | C12Q 1/005 205/792 |
| 2012/0077707 A1* | 3/2012 | Rapoport | G01R 33/30 506/12 |
| 2012/0088691 A1* | 4/2012 | Chen | B01L 7/52 506/12 |
| 2013/0023433 A1* | 1/2013 | Luo | C12Q 1/6841 506/9 |
| 2013/0143309 A1* | 6/2013 | Thomas | G01N 21/6486 435/287.2 |
| 2013/0234053 A1* | 9/2013 | Thomas | G01N 35/1011 250/573 |
| 2013/0295597 A1* | 11/2013 | DeWitte | G01N 35/08 435/23 |
| 2014/0300727 A1 | 10/2014 | Matthias et al. | |
| 2014/0320632 A1 | 10/2014 | Matthias et al. | |
| 2017/0138942 A1* | 5/2017 | Fan | B01L 3/502753 |

\* cited by examiner

DEVICE AND METHOD FOR DETECTING SUBSTANCES PRESENT IN BIOLOGICAL OR CHEMICAL SAMPLES

CROSS-REFERENCE TO RELATED APPLICATIONS

This application is a National Stage Application of PCT/EP2012/004526 filed Oct. 29, 2012, which claims priority to German Application No. DE 10 2011 117 320.3 filed on Oct. 28, 2011 and PCT/EP/2012/004490 filed on Oct. 26, 2012. Each of these applications is hereby incorporated by reference herein in its entirety.

FIELD

The present invention relates to an apparatus and a method for detecting the presence in biological or chemical samples of substances which deliver an optically detectable signal upon reaction with a reagent.

BACKGROUND

There is an ever increasing need for studies of biological and chemical samples. Often complete test series must be processed, and there is a requirement to do this in the most efficient way. For example, when implementing the so-called ELISA assay ("ELISA"="Enzyme-linked immunosorbent assay"), which is indispensable in clinical diagnostics and life science research, this needs to be done.

DE 10 2008 022 835 B3 describes a method and an apparatus that together form the basis for an analytical device for testing of biological or chemical samples, which upon reaction with a reagent deliver a detectable signal presenting as a color change and/or fluorescence as described in the preamble of claim 1 or 4, whereby ELISA tests can be executed. Here, a sample carrier (such as a microtiter plate) is used, usually in its multiple forms of two or more. These are receptacles for receiving samples. The receptacles may also be called indentations, slots, wells, or cavities. Downstream from the analytical device is an evaluation unit. This may, for example, be in the form of a photometer that is connected to a computer but is not directly part of the analytical device. This is used to study, analyze or evaluate the samples. Change in color, refers to any form of color alteration/shade.

It repeatedly happens that only very small quantities of sample fluids are available. In these cases it can be difficult to perform all the required analyses.

Additionally, a photometer requires different color filters to enable use with different sample types and reagents and the colors, color changes and reactions that result. Thus, when separate measurements with various filters are required, there is a delay in evaluation resulting from filter changes, which in turn also hinders the degree of automation possible.

SUMMARY OF THE INVENTION

The present invention aims therefore to overcome the above-mentioned disadvantages of the prior art and enable a resource-saving, sample use minimizing, evaluation that also makes optimal use of automation and accelerates the processes involved.

This task is achieved by an apparatus according to claim 1 and a method according to claim 4, a computer program product or computer program according to claim 10 and a data storage device according to claim 11 on which is stored a computer program product. Advantageous further developments of the invention are the subject of the dependent claims.

In the current invention, an apparatus for detecting substances present in biological or chemical samples comprises a sample carrier such as a microtiter plate, in which at least two sample receptacles such as indentations, slots, wells, or cavities etc. are provided, and in which each substance, on reaction with a reagent—preferably present as a liquid—yields an optically detectable signal. The exact form of this receptacle may vary greatly but plays no decisive role for the invention. In practice, there are mostly not only two, but many receptacles, typically arranged in standardized "footprints" or array patterns that are not invention limiting. Furthermore, according to the invention, the apparatus used for evaluation can be a camera (instead of downstream photometers as in DE 10 2008 022 835 B3), which may be for example a CCD camera and is preferably an electronic matrix camera, such as a CMOS camera. Whereby, the focal length, sharpness and distance settings are adjusted so that at least two receptacles are depicted in each individual image. It should be stressed here that the present invention is not limited to the capture by the camera of only a single image, but that it is self-evident that the camera can capture and accommodate multiple images for subsequent evaluation. Furthermore, the invention presented here also includes an evaluation device for evaluating the samples on the basis of images captured by the camera, whereby the color spectra contained in the image can be analyzed. Therefore different reagents, such as antigens and antibodies, may be added to the receptacle and lead to the presence of different signals such as fluorescence or color change that are captured with the camera in a single image, or by choice in multiple images, and then processed and evaluated by suitable software. In this manner, at least two measurable reactions taking place adjacent to each other within a single receptacle can be detected using a minimal sample volume, including but not limited to blood, serum, plasma or cellular fluid. In this way, it is possible to significantly reduce the sample (e.g. serum) volume while increasing the number of diagnostic parameters measured.

The other major advantage of the present invention is that only a single step is required for image generation and, that in this single step, signals or spectra generated by multiple reagents can be recorded. Additionally, only a single step is required for evaluation of a particular image with multiple spectra. The ability to simultaneously record and subsequently—where necessary with temporary storage of the image—(at least almost) simultaneously evaluate multiple spectra or signals together, in particular optical spectra, enables a higher throughput of samples and as a consequence increases the speed of processing. As no filter changes, or similar, are required, a higher degree of automation is achieved. Another advantage is the ability of the camera to capture and record completely different types of reaction within a single receptacle, i.e. fluorescence and optical color reactions can be recorded and analyzed. With the appropriate software, it is possible to perform and analyze these reactions in a single step and in a single apparatus.

As a general rule, there will be many, and at least more than two, receptacles within a sample carrier. This has the advantage that many different reagents can be placed in not just one, but many or all receptacles and these can be analyzed and evaluated together.

Furthermore, it is advantageous that the camera can acquire a single image of not just some of the samples present in the sample carrier, but all of them. This enhances efficiency and minimizes time-to-result, as well as improving the degree of automation.

According to the invention, the procedure for detection of substances present in biological or chemical samples that upon reaction with a reagent—preferably present in fluid form—deliver an optically detectable signal, may include the following steps: Initially, at least two (different) reagents are placed in each of at least two receptacles and sample is added. Using a camera (preferred is a CMOS camera), an image is generated such that at least two samples and their receptacles are pictured. Subsequently, the image is evaluated based on the signals generated by the interaction of the sample with the reagent, for example color spectra. Typically this involves use of the appropriate software and a computer. This procedure offers the same benefits as already described here for the apparatus. This is true for any preferred performance of the procedure. As a general rule, the signal is associated with a reagent and therefore the presence of a substance in the sample.

Preferably, at least two reagents will be placed in at least one part of the receptacle, whereafter an image of the receptacle is generated and then evaluated in a common, and therefore in many cases single, step.

In the context of the current invention, "addition of reagent(s) to a sample in a receptacle" can also be interpreted as "addition of a sample to reagent(s) present in a receptacle". The event of bringing to together of sample and reagent(s) is paramount, whereas the sequence of addition is not important.

Furthermore, it is an advantage when all samples in the sample carrier are presented in a single image and evaluated in a common processing step.

Typically and of benefit to the evaluation, the evaluation is performed by comparing an individual spectrum with a predetermined value/reference spectrum, preferably through comparison with a number of predetermined values/reference spectra. The reference spectrum or reference spectra are determined by generating one or more reference or baseline samples, present in one or more receptacles.

In another embodiment of the invention, the intensity of detected signals or signal is compared with the intensity of signals of known quantities of the, to be determined substance. Through assignment of the signal intensity, it is possible to quantitatively determine the amount of the substance in the sample.

In one practical implementation of the invention, the presence of substances within a particular sample is determined using classical immunological processes such as ELISA. In this way, and in accordance with the invention, simultaneous detection and quantification of different classes of antibodies or immunoglobulins such as IgA, IgM, IgG etc. can be performed. For this purpose, after binding the particular immunoglobulins to an immobilized antigen, at least one labeled antibody known to bind specifically to one of the immunoglobulin subclasses is added to the receptacle. By adding a mixture of differently labeled antibodies, each specific for a different immunoglobulin subclass, it is possible to generate a single image that can be used to compare the presence of the different immunoglobulin subclasses, enabling their differentiation within a single sample.

In a further embodiment, the invention can be used to characterize different cell types via appropriate labels, in particular color or fluorescence markers. For this purpose, the sample of interest, especially serum or plasma, is brought into contact with different labeled antibodies specific for specified cell types, in particular lymphocytes. By analysis using the camera, it is thus possible to define the cell populations present. Evaluation of color/fluorescence intensities can be used to provide semi-quantitative analysis of the cells present, in a manner similar to FACS (fluorescent activated cell sorting). The invention extends beyond the presence of specified cell types, as it can be used with cell fragments, cell organelles and/or other cell constituents.

Obviously, many different positional configurations of reagents within an individual receptacle are possible. These may be in the form of a square or rectangular matrix (or the major portion thereof) within the receptacle, as long as the number of reagents to be placed allows this. Alternatively, the reagents may be placed within the receptacle such that if numbers permit, they are so positioned that they are maximally apart from each other. It is also possible to position the different reagents on the floor of the receptacle such that they are in ordered forms such as concentric circles, or simply place them at random, where they remain attached and in a follow-up step, a sample such as blood or serum is added to the receptacle.

Another embodiment of the invention involves the use of a computer program product or computer program for a named evaluation device, a data storage device with a stored computer program product and the use of a camera for study of substances present in biological or chemical samples that deliver a color change or fluoresce after reaction with a reagent.

In accordance with the invention, the apparatus and/or procedure can also be used to control the volume of the sample or samples, prior to acquiring an image of one or more receptacles, in which one or more samples are present. Here, the camera can be swung or rotated away from the receptacle prior to image acquisition (e.g. at 90 degrees) such that it is directed at the boundary of the particular sample and the first fluid present in the pipette. Alternatively, the camera can be swung or rotated away from the receptacle prior to image acquisition (e.g. at 90 degrees) such that it is directed initially at one pipette and then at a second pipette, such that both pipettes are present together on a single image generated by the camera.

Thus, prior to acquisition of the image of the receptacle(s), the camera can be swung or rotated such that an additional image of the boundary between sample and first fluid (located within the pipette) or that the first and second pipettes are present on the same image.

In another embodiment, the camera is first directed vertically at the pipette or pipettes and then, following image acquisition, directed horizontally at one or more receptacles positioned under the camera. The apparatus and procedures required for image acquisition and evaluation of the acquired image of the boundary between sample and first fluid (located within the pipette) or the first and second pipettes such that they are present on the same image, as used in the current invention, is described separately in the applicant's parallel German patent applications with the application numbers DE 102011 117310.6 and DE 10 2011 117 323.8 (internal reference numbers AES 80204 and AES 80207 respectively) and considered through referral herein as disclosed and included in the current application.

Other advantages, features and characteristics of the invention result from the following description of the preferred, but not limiting, embodiments of the invention, based on the schematic and not true-to-scale drawings. These are not limitative thereof.

DETAILED DESCRIPTION

Figure 1:
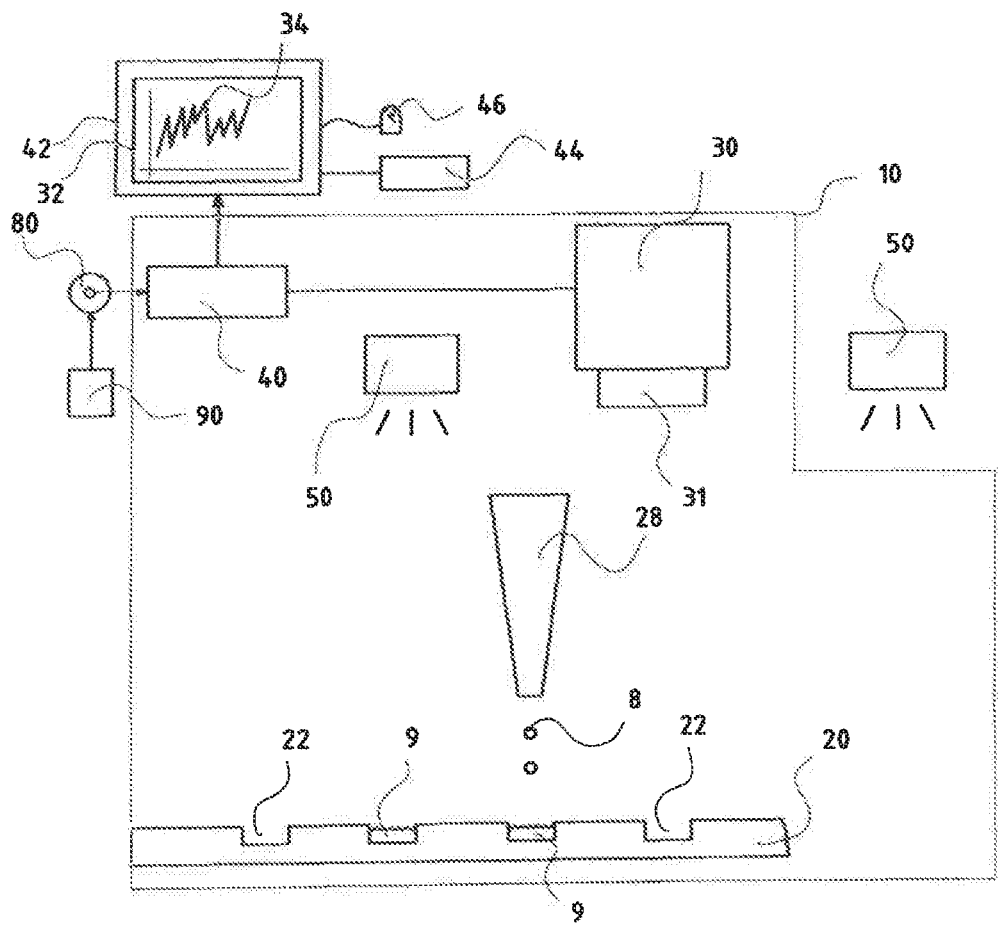
FIG. 1 heavily schematic illustration of side view of a model of the apparatus described in the invention, and FIG. 2 in top view, a model of the apparatus described in the invention.

FIG. 1 shows an apparatus 10 in accordance with the invention for study with biological or chemical samples which upon reaction with a reagent deliver a detectable signal presenting as a color change and/or fluorescence. The sample carrier 20 is envisaged to consist of multiple receptacles 22, in which samples 9 and reagents such as antibodies and/or antigens are placed, or can be placed. In order to assess for example the presence of certain substances in the samples 9, certain reagents 8 (represented here by drops 8) are added via pipettes 28 to the sample-containing receptacles 22. Whereby, a reaction of the samples 9 with the reagents 8 can cause release of optical signals such as color reactions or fluorescence. To ensure good illumination, lamps 50 are envisaged, of which two are shown as examples in this model.

To achieve an efficient, quick and automated evaluation of the reactions of the samples 9 with the reagents 8, the invention makes use of a camera 30 (especially a CMOS camera) that is placed such that the entire sample carrier 20 including all receptacles 22 is captured in a single image 32. It is self-evident that alternatively images 32 of parts of individual receptacles 22 can also be acquired and evaluated if required. In particular, this implies that the camera objective 31 has a suitable focal length that enables an appropriate distance setting.

The image 32 generated by the camera 30 is fed into a computer 40 that serves as the evaluation unit and the signals 34 contained in the image 32 are presented on a monitor 42. Typically, the computer can be controlled via a keyboard 44 and/or mouse 46. Using the computer 40 to run software or a computer program 90 (that can for example be stored on a CD 80) it is possible to evaluate the spectra acquired in the image 32 by comparing with reference spectra and/or reference values. According to the invention it is possible to evaluate all spectra simultaneously (or at least almost simultaneously). Each sample 9 and each receptacle 22 is automatically (e.g. through the use of barcodes) assigned to its correct spectrum 34 and the applied reagents (e.g. antibodies and/or antigens) are defined.

The resource-saving feature of the current invention involves adding two or more reagents 8 to an individual sample 9 present in an individual receptacle 22, whereby this could apply not just to a single receptacle 22, but also to multiple or all receptacles 22. It allows for simultaneous parallel detection of substances and where appropriate electronic storage. Evaluation of these signals using a database can be performed simultaneously or at a later stage.

Figure 2:
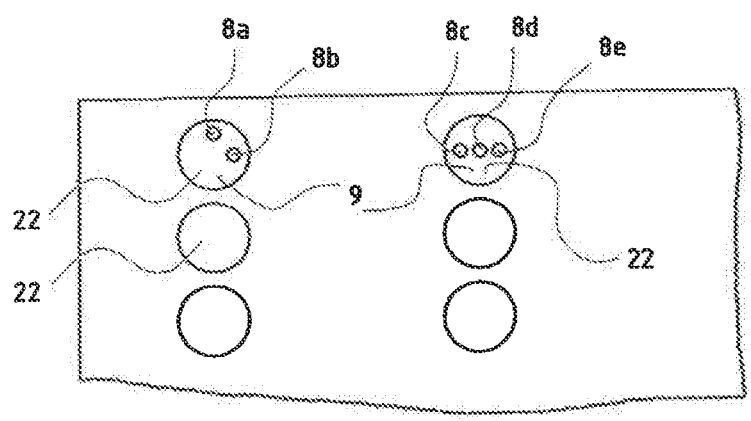

By way of example, FIG. 2 illustrates in top view a section through a sample carrier 20 with multiple receptacles 22 that each contain the sample 9. The receptacle 22 shown upper left in FIG. 2 had a first reagent 8 *a* and a second reagent 8 *b* added to the floor of the receptacle 22 prior to addition of the sample 9. The receptacle located top right had a third reagent 8 *c*, a fourth reagent 8 *d* and a fifth reagent 8 *e* added to the floor of the receptacle 22 prior to addition of the sample 9. By way of example, the three reagents 8 *c*-8 *e* in FIG. 2 have been added in a row.

Alternatively, the sample 9 (multiple different samples) can be added to the receptacle and reagents 8 can be added afterwards.

In a manner analogous to this, each individual receptacle 22 or a specific number of receptacles 22, can be occupied with multiple (different) reagents 8. After image 32 generation of the receptacle 22 with samples 9 and the reagents 8 *a-e*, the spectra can be evaluated as already described.

In this way, even the smallest quantities of sample fluids can be assessed for many different reactions. The use of even minimal quantities of sample fluids—such as blood, serum and cellular fluid—enables determination of many different parameters and diagnosis values by using differently measured reactions, so that the yield per sample volume is increased and the required sample volume is reduced. it is clear that the limitations of the method are linked to the optical resolution of the camera 30 and its objective 31, as well as the associated image processing and other factors such as possible mixing of reagents 8 in the individual receptacles 22.

With respect to evaluation, it should be mentioned that for quantification at specific locations (e.g. dots)—preferably in a row, column or line—reference substances will be positioned accordingly, so that standard dilution curves are produced.

For the record, with reference to the embodiments of the apparatus and procedures described as characteristics of the invention, including for example, execution of procedure and receptacle form, type of camera etc., other forms of procedures and apparatus may be used except when differently detailed or not permitted for technical reasons. It is clear, that the advantages and characteristics of the procedures described in the current invention are also valid for embodiments relating to the apparatus as described in the current invention and vice versa.

LIST OF REFERENCE CHARACTERS

8 Reagent
8 *a* First Reagent
8 *b* Second Reagent
8 *c* Third Reagent
8 *d* Fourth Reagent
8 *e* Fifth Reagent
9 Sample
10 Apparatus
20 Sample Carrier
22 Receptacle
28 Pipette
30 Camera
31 Objective
32 Image
34 Signal/Color Spectrum
40 Evaluation Device/Computer
42 Monitor
44 Keyboard
46 Mouse
50 Lamp
80 Storage Device/CD
90 Computer Program

What is claimed:

1. An apparatus for detection of substances present in a sample comprising:
    a sample carrier having multiple receptacles and barcodes, each barcode assigned to a respective receptacle and spectrum for a reagent positioned therein, each of the receptacles having two or more different reagents positioned therein, each of the reagents to react with a portion of the sample placed into the receptacle in which that reagent is positioned to release at least one optical signal via a color reaction or a fluorescence reaction, each of the reagents within each receptacle to evoke a different color reaction or fluorescence reaction from other reagents within the receptacle in which the reagent is positioned;

a camera positionable to capture a single image of the multiple receptacles of the sample carrier after portions of the sample are positioned in the receptacles and react with the reagents in the receptacles so spectra generated from the portions of the sample reacting with the reagents is detectable from the image; and an evaluation device to evaluate the sample through analysis of the spectra of the single image to detect different multiple substances within the sample via a comparison of only the single image with reference spectra and/or reference values and the barcodes.

2. The apparatus of claim 1, wherein the camera is configured to move relative to the sample carrier so that the camera is moveable away from the receptacles prior to image acquisition so that the camera is directed toward a first pipette from which at least one of the portions of the sample is positioned prior to image acquisition and is also moveable to be directed to the sample carrier to capture the single image.

3. The apparatus of claim 1, wherein the camera is movable vertically so that the camera is directable toward a first pipette in which at least one of the portions of the sample is positioned for depositing within at least one of the receptacles and the camera is also moveable horizontally so that the camera is directable toward the receptacles.

4. The apparatus of claim 1, wherein the camera is positionable for vertical and horizontal adjustment.

5. The apparatus of claim 1, comprising:
multiple pipettes positioned above the receptacles for depositing portions of the sample in the receptacles.

6. The apparatus of claim 1, comprising:
multiple pipettes positioned above the receptacles for depositing the reagents in the receptacles.

7. The apparatus of claim 1, wherein the reagents are different antibodies from different antibody subclasses.

8. The apparatus of claim 7, wherein the different antibodies are associated with specific color markers or fluorescence markers such that evaluation of color intensity or fluorescence intensity enables semi-quantitative analysis.

9. The apparatus of claim 8, wherein the reagents positioned in a first receptacle of the receptacles are spaced apart from each other and linearly aligned with each other.

10. The apparatus of claim 7, wherein the reagents positioned in a first receptacle of the receptacles are spaced apart from each other and are linearly aligned with each other.

11. The apparatus of claim 1, wherein there are at least three reagents positioned in a first receptacle of the receptacles, the at least three reagents positioned in the first receptacle being spaced apart from each other.

12. The apparatus of claim 11, wherein the at least three reagents positioned in the first receptacle are linearly aligned with each other.

13. The apparatus of claim 12, comprising:
at least one lamp positioned to illuminate the receptacles.

14. The apparatus of claim 12, wherein there are at least two reagents positioned in a second receptacle of the receptacles, the at least two reagents positioned in the second receptacle being spaced apart from each other, the second receptacle being spaced apart from the first receptacle on the sample carrier.

15. The apparatus of claim 14, comprising:
a display device connected to the evaluation device.

16. The apparatus of claim 15, comprising:
at least one input device connected to the evaluation device.

17. The apparatus of claim 16, wherein the evaluation device includes a computer.

18. The apparatus of claim 14, wherein, for each receptacle, the reagents positioned within the receptacle are spaced apart from the other reagents within the receptacle in a pre-selected matrix arrangement.

* * * * *